United States Patent [19]

Boehringer et al.

[11] Patent Number: 5,403,318
[45] Date of Patent: Apr. 4, 1995

[54] APPARATUS AND METHOD FOR SHAPING BONE

[75] Inventors: John R. Boehringer, Wynnewood; John Karpowicz, Glenmoore; Sean Kerr, King of Prussia, all of Pa.

[73] Assignee: Boehringer Laboratories, Inc., Norristown, Pa.

[21] Appl. No.: 163,358

[22] Filed: Dec. 6, 1993

Related U.S. Application Data

[63] Continuation-in-part of Ser. No. 5,887, Jan. 15, 1993.

[51] Int. Cl.⁶ ............................................. A61B 17/14
[52] U.S. Cl. .................................. 606/82; 606/79; 606/178
[58] Field of Search .................. 606/82, 79, 176, 177, 606/179; 30/123.3, 516, 515, 388, 392, 393, 394; 83/15, 22, 169, 170, 171

[56] References Cited

U.S. PATENT DOCUMENTS

| | | |
|---|---|---|
| 1,628,315 | 5/1927 | Hamilton . |
| 2,455,655 | 12/1948 | Carroll .................. 606/178 |
| 2,463,014 | 9/1949 | Bem ........................ 30/516 |
| 2,557,364 | 6/1951 | Treace . |
| 2,854,981 | 10/1958 | Morrison . |
| 3,554,197 | 1/1971 | Dobbie . |
| 4,008,720 | 2/1977 | Brinckmann et al. . |
| 4,148,236 | 4/1979 | Holoyen et al. ............ 83/74 |
| 4,513,742 | 4/1985 | Arnegger ................ 606/178 |
| 4,567,798 | 2/1986 | Brdicko .................... 83/71 |
| 4,664,165 | 5/1987 | Pollack et al. . |
| 4,729,763 | 3/1988 | Henrie ..................... 604/22 |
| 4,955,888 | 9/1990 | Slocum .................... 606/82 |
| 4,961,359 | 10/1990 | Dunham .................. 83/169 |
| 5,042,983 | 8/1991 | Rayhack ................. 606/87 |
| 5,084,971 | 2/1992 | Remington . |
| 5,087,261 | 2/1992 | Ryd et al. ................. 606/82 |
| 5,092,869 | 3/1992 | Waldron .................. 606/82 |
| 5,122,142 | 6/1992 | Pascaloff ................. 606/82 |
| 5,133,728 | 7/1992 | Petersen ................. 606/176 |
| 5,201,749 | 4/1993 | Sachse et al. ........... 606/177 |
| 5,306,285 | 4/1994 | Miller et al. ............ 606/177 |

FOREIGN PATENT DOCUMENTS

| | | |
|---|---|---|
| 768337 | 5/1954 | Germany . |
| 2427716 | 11/1975 | Germany .................. 606/82 |
| 162803 | 5/1954 | Sweden . |

*Primary Examiner*—Stephen C. Pellegrino
*Assistant Examiner*—Guy V. Tucker
*Attorney, Agent, or Firm*—Paul & Paul

[57] ABSTRACT

Apparatus and method is provided for shaping bone, in which a cooling, lubricating and/or curative fluid is delivered by means of the shaping member, in order to cool or lubricate the shaping member where it contacts the bone and/or to provide a curative fluid to the shaped surface of the bone. Preferably, the cooling fluid is at least partially water, with or without a curative substance carried therein, with the liquid being delivered at the shaping end of the member, in a direction toward the shaped bone. The fluid may be provided through the interior of the shaping member to at least one relatively narrow opening located at the shaping end of the member, or may be provided by at least one exterior channel that runs along at least one wide side of the shaping member. Optionally, cooling liquid may also be delivered through the interior of the shaping member for discharge through at least one narrow side thereof. A porous medium that allows for controlled flow of lubricating fluid may also be provided on at least one wide side surface of the shaping member.

14 Claims, 7 Drawing Sheets

APPARATUS AND METHOD FOR SHAPING BONE

CROSS-REFERENCE TO RELATED APPLICATIONS

This is a continuation-in-part of U.S. Patent application Ser. No. 08/005,887, filed Jan. 15, 1993, still pending.

BACKGROUND OF THE INVENTION

This invention relates to the shaping of bone. One technique of bone shaping is by resort to a saw, often an oscillating saw, but it will be understood that, in the broadest context, this invention relates not only to the sawing of bone, but also to various types of other abrading such as burr removal, reaming, grinding, cutting, milling, drilling, scraping, and even to electro-surgery and laser cutting devices.

Typically, such shaping equipment is used in orthopedics, and most often involves the use of saws to machine off portions of bone to fit prosthetics such as are used, for example only, in artificial knees and hips. Such shaping apparatus, often saws, are also used to cut pieces of bone out of hip sites, in order to form or shape a splice or fixation piece for operations on the spine, for example. Such pieces of bone must be extensively sawed and milled to shape.

In the course of such operations, the death or necrosis of bone tissue can be experienced any time the temperature resulting from shaping exceeds 130° F. for any significant period of time. When such necrosis occurs, the tissue does not grow into the cut site, fracture site, or surface of the cementless prosthesis or other prosthesis and may fail to knit. In the absence of knitting, the prosthesis may not be anchored by bone growth, possibly resulting in the necessity to have a replacement operation some period of years thereafter, often called a "revision procedure." In some instances, half of all knee or hip operations may be revision procedures, often because in the initial operation, where temperature is a contributing factor, excessive temperatures were reached at the site of the shaped surface or bone kerf (or cut). Furthermore, in the absence of lubrication, small metal particles may be abraded from the saws and remain in the wound where they adversely affect long term viability of the tissue.

It has in the past beenerecognized that it would be desirable to cool the shaping devices during their operation, in order to keep heat build-up at a minimum. To such an end, it is known to apply fluid such as water to the tool by external means, such as by a syringe, in order to attempt to cool the tool at the shaping site.

U.S. Pat. No. 2,557,364 represents a prior art surgical saw blade.

U.S. Pat. Nos. 4,008,720 and 5,087,261 represent bone saws of the type in which an oscillating blade driver drives a bone saw in an oscillating motion, and in which means are provided for delivering a cooling liquid to the bone site. Such prior art devices either do not deliver cooling liquid directly to the cutting site, or provide limitations in the type of shaping member due to the manner of liquid delivery. In one known blade, nearly one third of the cutting tooth edge is removed to provide a conduit for the fluid.

It has also been found in connection with the shaping of bone, and particularly where a liquid is provided during such bone shaping for purposes of cooling the saw or other shaping member, that sprays or aerosols are generated. Such generation of sprays (or aerosols) at the site of the shaped bone (or kerf) create dangerous conditions, because of the dissemination of infections that might be present in the bone tissue, to the medical personnel attending the operation. For example, such infection might include hepatitis, AIDS, or the like. Prior art bone shaping apparatus and methods do not appear to have effectively addressed this serious concern.

To the extent that the prior art appears to have addressed the prevention of the dissemination of aerosols having the effluent of bone shaping, such as blood and tissue therein, such have generally proven to be inadequate. For example, mechanical barriers, such as transparent screens, may be provided, but visibility may be partially blocked as aerosols land on the screens, and such lack of visibility becomes detrimental to the operation. Consequently, in many cases, mechanical barriers are not utilized, and the medical personnel may often be observed with red, moist aerosol-caused accumulations of blood and tissue on their gowns, masks and caps, at the end of an operation.

U.S. Patent application Ser. No. 08/005,887, of which the present application is a continuation-in-part, and which is incorporated herein by reference, discloses a bone shaping device in which cooling liquid is provided through one or more conduits with openings located at the narrow sides of the shaping member. Application Ser. No. 08/005,887 also discloses an apparatus and method for containment of aerosols generated at the site of the bone shaping operation in which a gaseous fluid such as air impinges with the aerosols in order to drive the aerosols away from the shaping apparatus and toward the bone.

THE PRESENT INVENTION

The present invention is directed to providing a bone shaping apparatus comprising a shaping member that includes a fluid conduit having at least one opening of specified configuration located at the shaping end of the member, directed toward the portion of the bone being shaped and in fluid communication with the cut surface.

The present invention is also directed to providing a bone shaping apparatus comprising a bone shaping member including a fluid conduit that opens through a porous material located at at least one wide side surface of the shaping member to provide lubrication between the shaping member and a fixture which locates and guides the saw.

The present invention is also directed to providing a bone shaping apparatus including a shaping member having an external channel located on at least one wide side surface of the member for delivering fluid to the shaped bone surface and for removing fluid and cuttings from the bone shaping area.

The present invention is further directed to providing additional liquid along the shaping member, at one or more of its narrow sides, through one or more conduits in the narrow sides, opening toward the abraded bone surface.

SUMMARY OF THE INVENTION

It is an object of this invention to provide an enhanced fluid delivery technique and apparatus for a bone shaping operation.

It is another object of this invention to provide a bone shaping apparatus comprising a shaping member that includes a fluid conduit having at least one relatively narrow slot located at the shaping end of the member, and directed toward the portion of the bone being shaped.

It is a further object of this invention to provide a bone shaping apparatus comprising a bone shaping member including a fluid conduit that opens through a porous medium located at at least one wide side surface of the shaping member to provide lubrication.

It is another object of this invention to provide a bone shaping apparatus including a shaping member having an external channel located on at least one wide side surface of the member for delivering fluid to the shaped bone surface.

It is a further object of this invention to provide a saw of superior tooth configuration in which the teeth are disposed along a concave arc to promote higher cutting load per tooth and improved lubrication and clearing of the teeth.

Other objects and advantages of the present invention will be readily apparent upon a reading of the following brief description of the drawing figures, the detailed description of the preferred embodiments, and the appended claims.

BRIEF DESCRIPTION OF THE DRAWING FIGURES

DETAILED DESCRIPTION OF THE PREFERRED EMBODIMENTS

Figure 1:
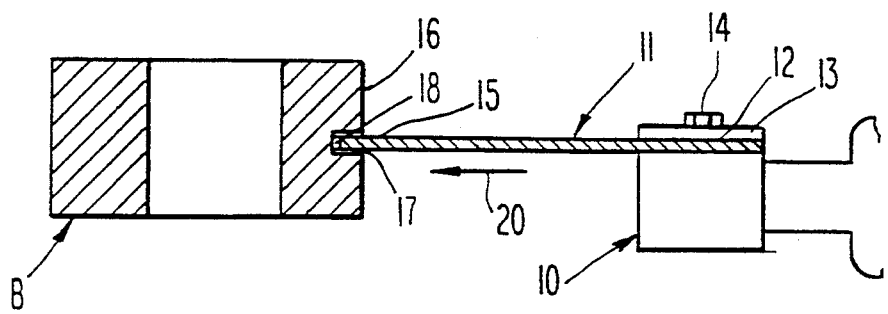
FIG. 1 is a schematic vertical sectional view, taken through a shaping apparatus of the bone saw type, showing a bone kerf being cut into a bone, with the tool being driven by a suitable oscillating driving apparatus, fragmentally illustrated, which tool is typical of prior art bone shaping apparatus.

Referring now to the drawings in detail, reference is made to FIG. 1, wherein a shaping apparatus is shown, of a type that is representative of the prior art, and in this instance, the same is shown as a bone saw apparatus. The saw apparatus will having a driving mechanism 10 which in the case of a bone saw, will preferably drive the saw member 11 in an oscillating motion, such as for example, similar to those disclosed in any of the above-mentioned patents, or for example, in U.S. Pat. No. 2,854,981, with the right-most end of the bone saw 11 being connected to the oscillating tool 10 at its end 12, by means of a suitable end plate 13 and fastener 14.

The bone B is shown to the left of FIG. 1, with the left end 15 of the saw penetrating the surface 16 of the bone B to form a groove, indentation or the like, normally called a bone kerf 17, as the teeth 18 at the left end 15 of the saw 11 penetrate the bone B, moving leftward, or in the direction of the arrow 20 in FIG. 1.

Figure 2:
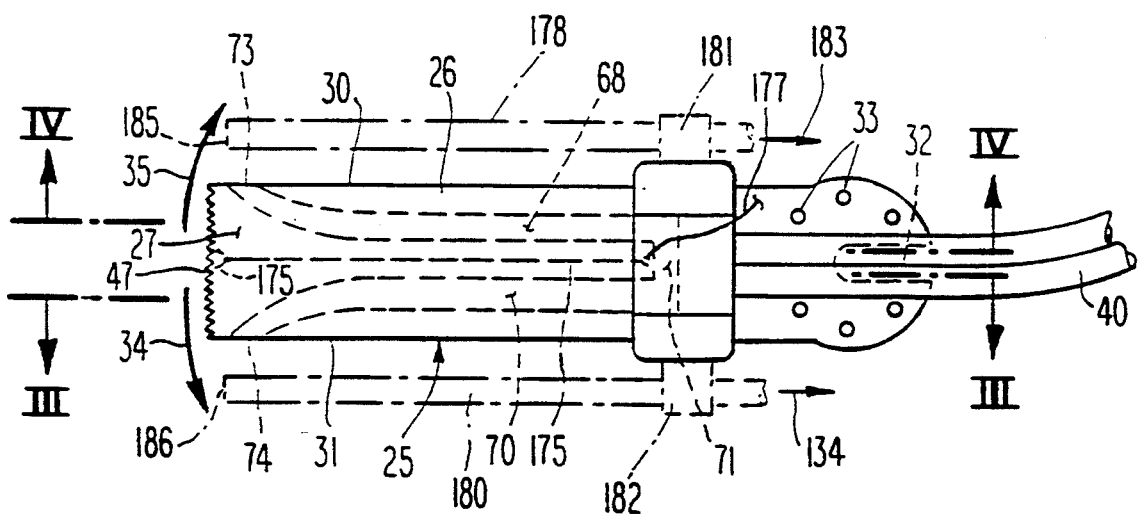
FIG. 2 is a top plan view of a bone shaping apparatus of the bone saw type, wherein liquid cooling conduits within the bone saw are illustrated in phantom, and wherein scavenging conduits for scavaging away the results of bone shaping are likewise illustrated in phantom, on opposite sides of the full line illustration of FIG. 2.

Referring now to FIG. 2, a shaping apparatus in the form of a bone saw, in accordance with this invention, is provided, generally designated by the numeral 25. The shaping apparatus 25 includes a shaping member 26, which in this particular embodiment of the invention in which the shaping member is a bone saw, comprises a generally flat saw blade, having wide top and bottom surfaces 27, 28 connected by narrow side surfaces 30 and 31.

The right or first end of the shaping member 26 is provided with a suitable slot 32 for attachment to the driving source or tool 10, and preferably with a plurality of bolt holes 33, for also assisting the securement of the same to a tool 10, whereby fasteners, bolts or the like may be received within the holes 33, and whereby after such attachment to a suitable driving source, the saw-type shaping apparatus 25 may be oscillated backwards and forward, in the directions of the arrows 34, 35 of FIG. 2. In the alternative to bolt holes 32, one or both major surfaces of the end 12 of the saw may be roughened, as by means of a frit-covering, or even a knurling for high frictional gripping or clamped engagement between the drive 10 and its end plate 13, with the end 12 of the saw therebetween.

Figure 3:
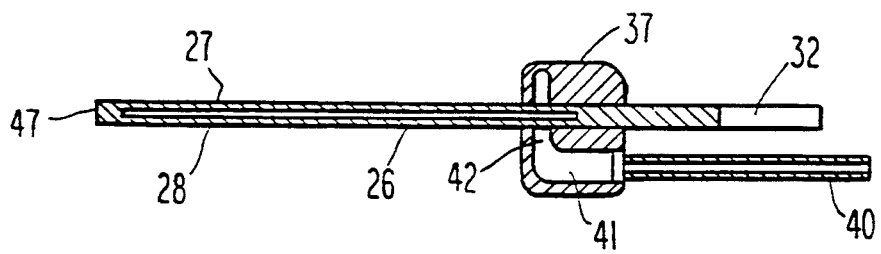
FIG. 3 is a vertical sectional view, taken through the apparatus of FIG. 2, generally along the line III—III of FIG. 2, and wherein gaseous fluid and liquid fluid delivery means is illustrated, via a manifold means.
Figure 4:
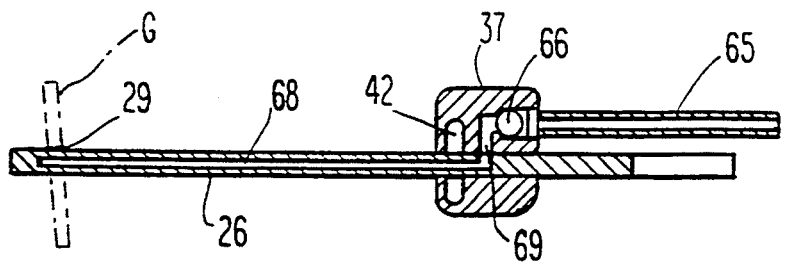
FIG. 4 is a view similar to that of FIG. 3, but taken along the line IV—IV of FIG. 2, and wherein the liquid delivery valve means is also illustrated.

The apparatus 25 includes a manifold member 37 extending above and below the surfaces 27, 26, respectively of the saw blade member 26, as shown in FIGS. 3 and 4, connected thereto by suitable means (not shown). The manifold 37 is a manifold for both gaseous fluid (preferably air) and liquid fluid (often water, with or without additives thereto, the most common of which is a saline solution). In accordance with conventional terminology, element 37 is termed a "manifold" because fluid that enters the interior chamber thereof is directed to a plurality of fluid exit locations.

Figure 6:
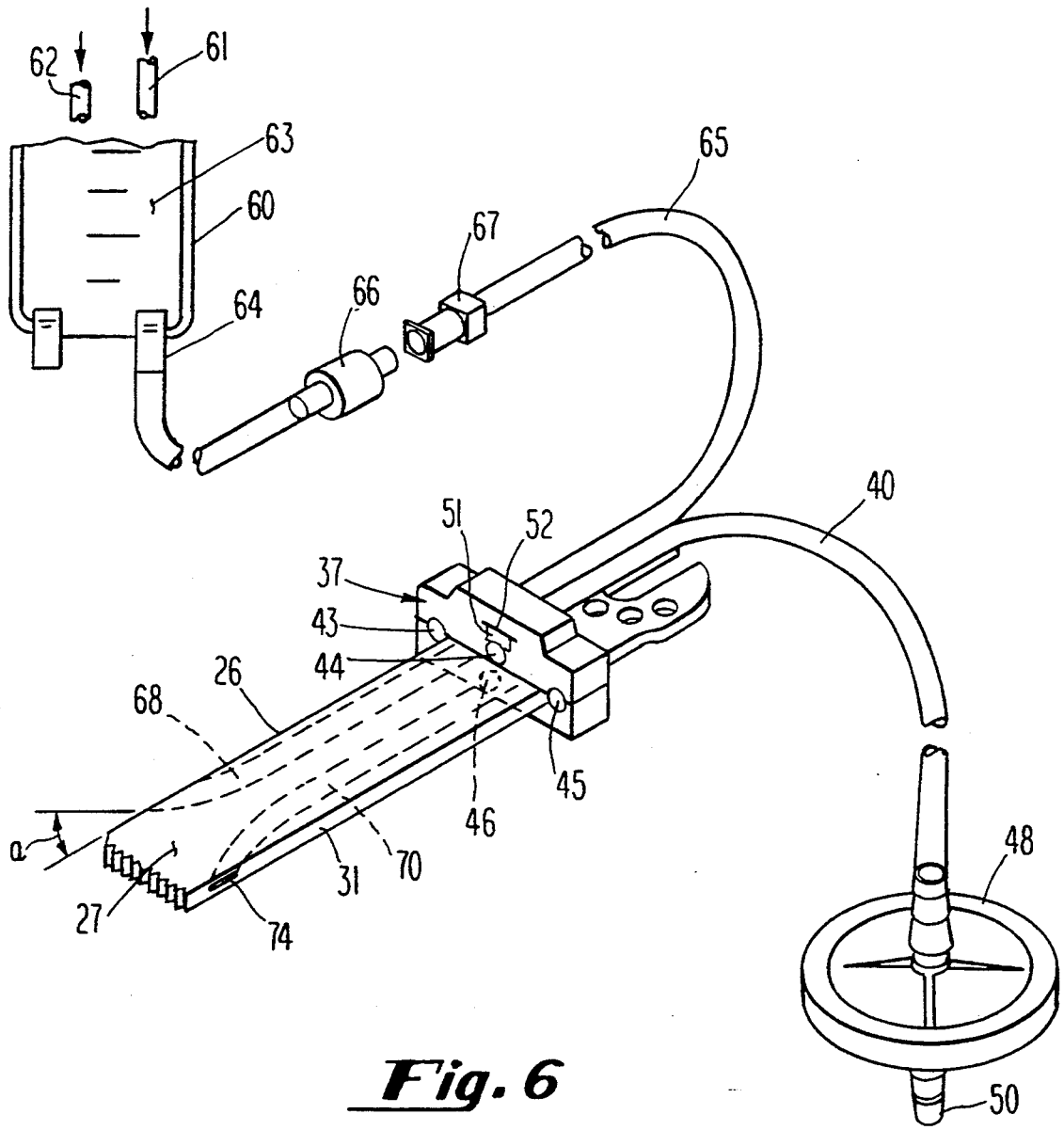
FIG. 6 is a top perspective view of a shaping apparatus, with gaseous fluid and liquid fluid delivery conduits thereto being illustrated.

With reference to FIG. 3, in particular, it will be seen that means are provided for supplying a source gaseous fluid, such as air, such means being in the form of a tube or like 40, which delivers the fluid to a zone 41 in manifold 37, which zone, in turn, is in communication for delivering the gaseous fluid into an upwardly extending zone 42 of the manifold, for discharge from the front (or left as viewed in FIGS. 3 and 4) of manifold 37 via upper and lower openings 44, 46, disposed, respectively, just above and below respective upper and lower saw blade surfaces 27, 28, as is more clearly shown in FIG. 6, in the direction of the second, or left-most end of the blade 26, at 47, where the saw teeth of the blade 26 are located.

Similarly, openings 43 and 45 are provided, as shown in FIG. 6, for discharge of gaseous fluid, preferably air, along respectively associated narrow side edges or walls 30, 31 of the shaping blade 25.

It is the discharge of gaseous fluid, preferably air, from tube 40 via zones 41, 42, and outwardly of the openings 43–46, that enables the formation of a moving air curtain, directing the air (or other gaseous fluid) away from the manifold 37, and along the blade 26, toward the teeth 47, which, in use, would be toward the bone kerf, such as that 17 in the bone B of FIG. 1, in operation. The curtain could be oxygen, if desired, to improve local oxygenation at the site of shaping. It is the curtain thus formed which enables the impingement of the same with aerosols (or sprays) emanating from a bone kerf as it is being abraded, to be continually urged back toward the bone kerf, and away from the surgeon or other medical professional generally handling the shaping apparatus 25, from the right end thereof, as viewed in any of FIGS. 2–6.

The air provided to the tube 40 will ordinarily have already passed through a bacteria filter, such as the 0.2 micron bacteria filter 48, shown in FIG. 6, which, in turn, is connected to a suitable air or other gaseous fluid supply, as at 50, to provide connection to a source of pressurized air.

It will be noted that the openings 43, 44, in particular, with an oscillating or pivotal movement of the blade 26 as shown in FIG. 2, serve to sweep the sides of the blade 26 throughout the arc provided by the oscillation, as the saw cuts bone.

It will also be noted that a baffle or deflector 51 is provided, pivotally mounted along one edge 52 thereof, as shown in FIG. 6, to partially overlie the opening 44, to provide adjustable positioning for the baffle 51 partially across the opening 44, so that some deflection of the stream of gaseous fluid, preferably air, from the opening 44, may be provided, to facilitate adjustment of the air curtain provided thereby. Similarly, the other openings 43, 45 and 46 may likewise be provided with a baffle or deflector 51, adjustably positionable partially thereover, if desired, although the same is not shown. In this manner, fine adjustment of the gaseous fluid curtain can be provided along all sides of the blade 26.

With reference now to FIGS. 2, 4, 4A and 6, it will be seen that liquid fluid, preferably an aqueous medium, a physiological balanced salt solution, or a saline solution or the like, if desired, generally containing some water is provided at 60, preferably from a delivery source, as 61, for water or the like to moisten the bone, and a secondary source 62, for delivery of an additive to the solution 63 in the container 60, if desired, which additive may function as an antibiotic substance, or a solution to help promote bone growth, to help nourish and protect the fresh cut surface, the same being provided via line 62 into the container 60, as shown in FIG. 6 or the like. The discharge end 64 of the container 60 passes the liquid to line 65 via suitable connector fittings 66, 67, preferably of the quick-connect/disconnect type, whereby the liquid fluid, preferably water, is delivered to the manifold 37 via the line 65, which delivers the liquid to the manifold 37 through valve 66. After passing through valve 66, the liquid passes downwardly via vertical conduits 69, to enter horizontally conduits 68, 70 running substantially the length of the blade 26 from the manifold 37, to the left, or second, end of the blade 26 as shown in FIG. 4, and as shown in phantom in FIG. 2, being fed via feeder conduit 71 as shown in,FIG. 2. The discharge of the conduits 68 and 70 from the saw blade 26, is via openings 73, 74, respectively, shown in FIGS. 2 and 6, in the short or narrow sides 30, 31 of the blade that connect the wide sides 27, 28 thereof, in transverse cross-section.

Figure 4A:
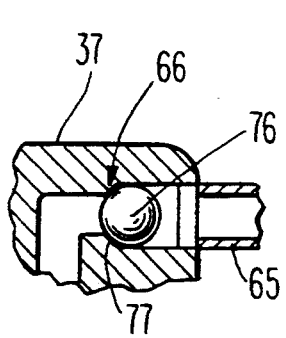
FIG. 4A is an enlarged fragmentary vertical sectional view of the valve illustrated in FIG. 4, shown enlarged for purposes of clarity.

With particular reference to FIG. 4A, it will be seen that the valve generally designated by the numeral 66, in the manifold 37, to which pressurized fluid, such as water or the like, is provided via line 65, comprises a ball 76, generally urged in seated engagement against a valve seat 77, by liquid pressure provided in line 65. The weight and size of the ball 76 may be selected, with due regard to such pressure, and with due regard for the amount of vibration that is set up upon oscillation of the blade when in use, such that such oscillation will normally cause the ball 76 to become unseated during operation of the tool due to such vibration, but that, when the tool is not operating and no oscillation occurring, the water pressure will again cause the ball 76 to seat against the valve seat 77.

Figure 5:
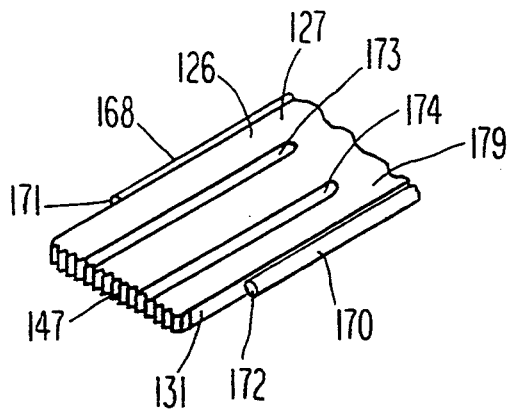
FIG. 5 is a fragmentary, top perspective view of an alternative liquid delivery system, along the sides of a saw blade, and with grooves being provided in the blade for discharge of products of the shaping operation, therealong and/or for heat dissipation.

With reference to FIG. 5, it will be seen that an alternative blade 126 is provided, with teeth 147, and wherein conduits 168, 170 are provided on opposite narrow sides of the blade, rather than running down through the inside of the blade 126, as an alternative embodiment, with such external conduits 168, 170, terminating in liquid openings 171,172, otherwise functioning in the manner of the conduits 68, 70 of FIG. 6.

In the embodiment of FIG. 5, it will be noted that grooves 173,174 appear on the top surface 127 of the saw blade 126, and the same kind of grooves appear on the lower surface (not shown), in order to facilitate the passage of liquid and solid debris to or away from the bone kerf, or other shaped surface during cutting operations, with such particles of residue as a result of the bone shaping thereby being capable of being moved away from the kerf, or site of operation.

It will also be noted that an air curtain similar to that provided via the gaseous fluid delivery system of FIGS.

2-4 is provided in the embodiment of FIG. 5, and that such curtain, particularly those portions thereof emanating from openings along the narrow sides 130, 131 of the blade 126, facilitate even further the guidance of liquid delivered via openings 171, 172, into the cut or kerf provided in the bone, just as air or other gaseous fluid delivered via openings 43, 45 in the embodiment of FIG. 6, facilitates the delivery of liquid discharged via openings 73, 74, in the embodiment of FIGS. 2 and 6.

With reference to FIG. 2, it will be seen that a sensor 175 is shown in phantom, embedded in the left-most end 47 of the blade, such sensor being adapted to record temperature, pressure, force, or sound, or any other desire parameter that corresponds to the shaping or cutting of the bone, during the bone shaping operation, and that the signal thus picked up by the sensor 175 is delivered via a signal delivery line 176, inside the saw blade 26, to a suitable exterior signal delivery line 177, to a suitable recordation device (not shown) for purposes of monitoring desired parameters during the shaping operation, and adaptive control of the shaping process.

It will also be noted, with reference to FIG. 2 that scavenging conduits 178, 180 may be provided, as shown in phantom in FIG. 2, carried by suitable respective mounting bosses 181, 182, that in turn are carried by the manifold 37, and that a suitable source of partial vacuum is provided to the conduits 178, 180, to create a suction or drawing effect in the direction of the arrows 183, 184, whereby liquids, with or without solid particles, such as bone debris and the like, may be withdrawn from the site of the operation, via scavenging inlet openings 185, 186, to discharge, in order to clear the kerf or other area around the operation, for greater visibility of the operating personnel, for better treatment of the operating site, or both, as may be desired. It will be understood that the scavenging apparatus 178, 180, 181, 182, are optionally provided, and may be provided carried by the shaping apparatus 25 of this invention, or may be separate therefrom.

It will also be understood, while the means for generating the air curtain is preferably carried in the manifold 37 as described above, that such may, if desired, be provided in a separate fixture, rather than being specifically carried by the apparatus 25, as shown in FIGS. 2 and 6.

It will also be noted that the saw-tooth end of the blade 47 may be provided integral with the blade 26, or may be a separate member attached thereto. In the case where the same may be a separate member, such may be done in instances in which it is desired that the cutting teeth be constructed of a material different than that of the remainder of the blade such as diamond, carbide or the like.

It will thus be seen that with the present invention, the part of the saw blade that is closest to the surgeon may be kept relatively dry and free of aerosols, in that the air openings blow water and small particles, such as aerosols, away from the user. It has been found that, with the device of the embodiment of FIGS. 2-6, for example, the side openings 43 and 45 are particularly effective to blow larger particles toward the bone and blow water away from the surgeon, and that upper and lower openings 44 and 45 produce a coanda effect to blow small particles and aerosols, as well as water, away from the surgeon or other user.

It will also be noted that, with particular reference to FIG. 6, the angle of discharge of liquid from the blade, along the narrow edges 30, 31 of the blade, will preferably be at an angle "a" of 30° or less to provide a forward component of motion for liquid being discharged from the blade, to facilitate driving the liquid toward the bone. As aforesaid, the air from openings, such as the opening 43, 45, likewise facilitates driving the liquid to the bone. It will further be noted that, if desired, the water or other liquid channels 68, 70 could be pressurized and/or pulsed (not shown), to have air behind them, to drive the water to the bone with greater force, or in a pulsing manner, and that such air being driven to the bone could be instead of, or in addition to air provided via the manifold 37 as shown in the illustrated embodiments. One way to provide air pressure behind the liquid would be to have the tubes 40, 65 interconnected, or to provide fluid communication between zones 42, 68.

It will further be noted that, while not shown in the embodiments illustrated, suitable shut-off controls may be provided for the air flow, either in the conduit 40, or within or on top of the manifold 37, to control the air flow in the blade, either by adjustment, by shut-off valve, or the like, as may be desired. In this regard, the control could occur in the form of a ball valve or the like, similar to that shown in FIG. 4A for liquid shut-off, at the inlet of the line 40 to the manifold 37 in FIG. 3, similar to that shown in FIG. 4, if desired.

In FIG. 4, there is also shown a saw guide "G", in phantom, having a slot 29 through which the blade 26 fits with minimal clearance, with the slot 29 having one side spring loaded (not shown) or otherwise constructed to maintain the clearance between the slot and saw to a minimum, to eliminate rocking of the saw in the guide, when the saw is in use and the guide is disposed against the bone B, clamped thereto or otherwise, as desired.

Similarly, adjustments for liquid and/or gaseous fluid supplied via the apparatus 25 may be controlled in a variable amount, or in an on/off manner, either manually, or by means of the sensing of any of a number of parameters via sensor 47, or in any other manner.

Furthermore, it will be noted that, particularly for, but not limited to, a shaping tool of the bone saw type, as illustrated herein, the larger surfaces 27, 28, but even, if desired, the narrower surfaces 30, 31, could be provided with a friction reducing coating 179, such as tetrafluoroethylene, to minimize friction as those surfaces interact with surfaces of bone, in cutting the bone kerf.

Generally, the surfaces of the saw blade are hardened, and most preferably are hardened steel. The hardening may be accomplished by any of various techniques, such as by nitriding, by neutron bombardment, or any other hardening, particularly surface hardening techniques known in the metalurgical arts.

Additionally, with particular reference to the embodiment of FIG. 5, it will be seen that the grooves 173, 174, whether or not used to partially carry away liquids and entrained solids from the site of operation, may also be effective as relieving grooves, to minimize heat that might otherwise be generated in the upper and lower (or larger) surfaces of the blade.

Additionally, while in the embodiments shown, the teeth 47 are illustrated as conventional saw-tooth cutting teeth, it will be understood that some tooth geometries provide better working conditions than others, particularly in an environment in which liquid is being provided for cooling purposes.

In practicing the present invention, it will be understood that, particularly where liquids are scavenged, as for example via lines 178, 180, such allows the option for collection of the liquid, its filtering and re-use, if desired.

It will also be noted that the liquid coolant provided to line 65, in addition to being water, or a water solution such as saline solution, may be provided with other treatments, such as antibiotics, lubricants, anti-foam agents, agents that may produce foam, wetting agents to facilitate cooling provided by the liquid, thickeners and thinning agents for the liquid, or the like, all within the spirit and scope of the invention.

Figure 7:
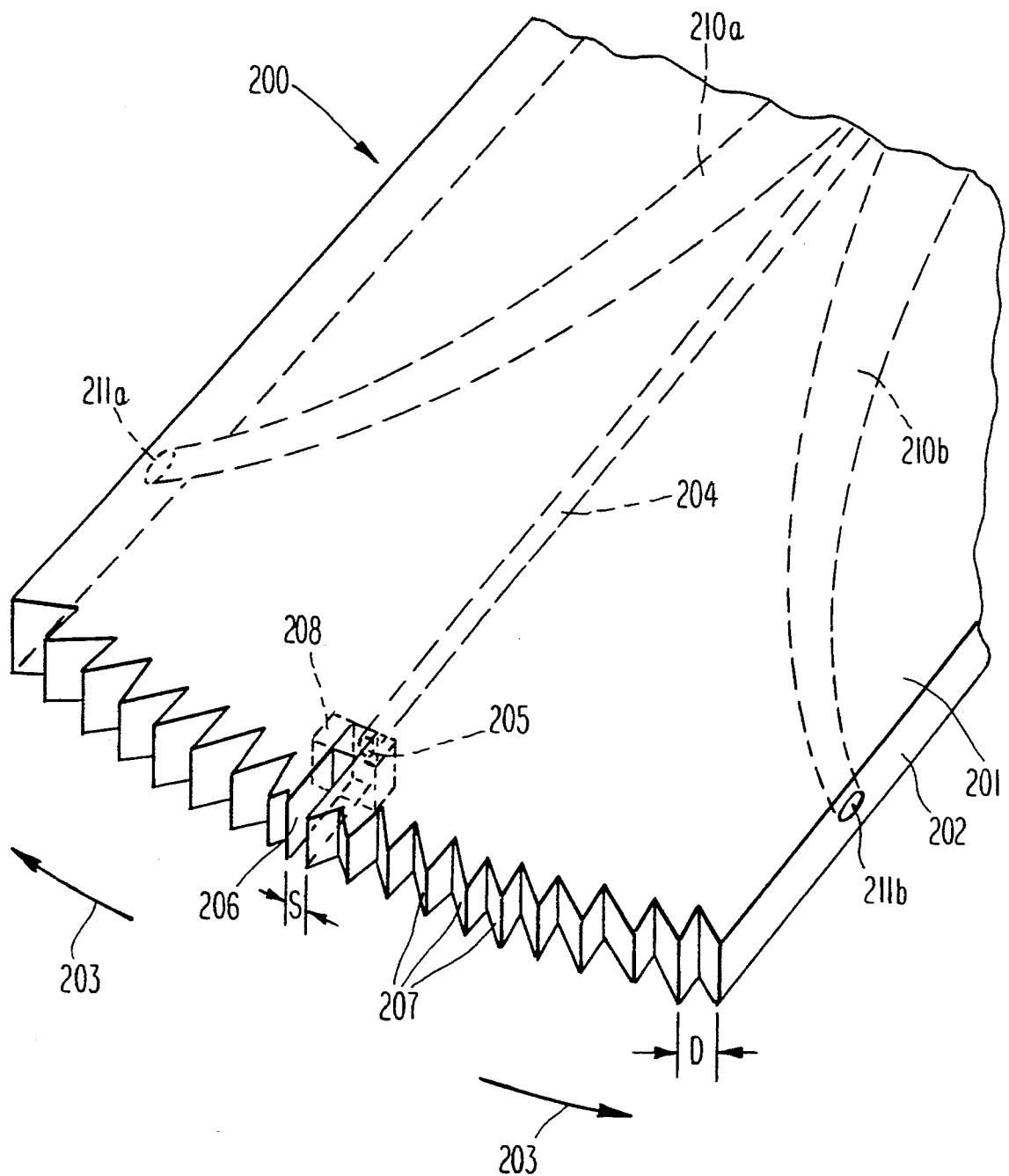
FIG. 7 is a fragmentary top perspective view of a shaping apparatus in accordance with the present invention, with multiple fluid delivery conduits for providing the same or different types of fluid to a shaped bone surface.

FIG. 7 is a top perspective view of a shaping member in accordance with one embodiment of the present invention.. The bone shaping member 200 comprises two wide sides, one of which is shown as element 201, connecting two, narrow sides, one of which is shown as element 202. The shaping member 200 is adapted for oscillating shaping or cutting motion in a direction as illustrated by the arrows 203. A first conduit 204 shown in phantom extends through the center of the shaping member in a direction perpendicular to the transverse cross-section of the shaping member. The conduit 204 is shown as having a circular cross-section, however, any other suitable cross-sectional shapes such as square, rectangular, etc. may be used. The cross-section of the conduit 204 preferably has an aspect ratio of about 1:1 in order to provide a relatively concentrated fluid stream of sufficient pressure when connected to a suitable fluid source, while at the same time reducing the amount of material that must be removed from the interior of the blade. Thus, sufficient fluid may be supplied through the conduit 204 while maintaining improved structural rigidity of the blade. The conduit 204 opens at 205 into a slot 206.

In FIG. 7, the slot 206 extends the entire length between the wide sides of the shaping member in a direction perpendicular to the plane of the wide sides. The width of the slot 206 is relatively narrow, having the dimension S as shown in FIG. 7. The bone shaping member 200 comprises a series of shaping or cutting teeth 207 disposed at the shaping end thereof. The spacing distance of the teeth 207 is shown by the dimension D in FIG. 7. The width S of the slot 206 is shown as being narrower than the spacing distance D of the teeth 207. In a preferred embodiment, this configuration maintains the total edge area of the cutting teeth by providing only a minimal area in which the teeth gullets are interrupted by the slot 206. In addition, this configuration substantially prevents bone fragments from becoming trapped in the slot during operation of the apparatus, thereby eliminating clogging of the fluid supply. As shown in FIG. 7, the slot 206 is preferably located in the gullet between two cutting teeth, which provides no interruption in the spacing of the blade portions of the teeth 207. The slot 206 preferably extends length-wise a short distance away from the cutting members 207 such that the end of the conduit 205 is recessed a short distance from the cutting surface. This configuration, as shown in FIG. 7, minimizes clogging and also allows cooling, lubricating and/or curative fluid to be directed against both the cutting surface contacted by the teeth 207 and the cut bone surface contacted by the wide sides 201 of the bone shaping member. Alternatively, the end of the conduit 205 may be provided flush with the cutting teeth 207. In this case, the end of the conduit 205 is preferably located in the gullet between two adjacent cutting teeth.

As shown in phantom in FIG. 7, a porous dispensing medium 208 may be secured within the slot 206 to control the flow of fluid as it exits the end of the conduit 205. The porous medium 208 may be used to optimize the amount of fluid distributed to the wide surfaces 201 of the shaping member and to the cutting surface of the teeth 207.

As shown in FIG. 7, a second set of conduits 210a and 210b, shown in phantom, may be provided in the shaping member 200. The conduits 210a and 210b open through openings 211a and 211b, respectively, located on the narrow sides 202 of the shaping member. The conduits 210a and 210b are connected to a fluid source as described above and are used to direct cooling or other fluid towards the shaped bone surface. The fluid provided through the conduits 210a and 210b may be the same or different fluid as that provided through the conduit 204. The conduit 204 may be connected to a separate fluid source from the conduits 210a and 210b, whereby the ability exists to provide a different type of fluid or a different rate of fluid flow through the conduit 204. For example, conduits 210a and 210b may be used to supply cooling liquid to the shaped bone surface while conduit 204 may be used to supply additional cooling fluid and/or a curative fluid to the shaped bone surface. Thus, when a curative solution is applied through the conduit 204 and a cooling solution is supplied through the conduits 210a and 210b, a surgeon can select to use only the cooling fluid on a first cutting pass and the curative fluid on a second pass. Alternatively, the surgeon can select to provide the cooling and curative fluids simultaneously on a single pass.

When cooling fluid is provided through each of the conduits 204, 210a and 210b, very effective cooling of the shaped bone surface is achieved due to the multiple areas in which fluid is delivered. When cooling fluid is provided only through the conduit 204, effective cooling is also achieved because the cooling fluid is applied directly to the freshly cut bone surface. While a single slot 206 is shown in the end of the shaping member 200 in FIG. 7, multiple slots or other openings may be provided at varying locations along the end of the shaping member 200.

Figure 8:
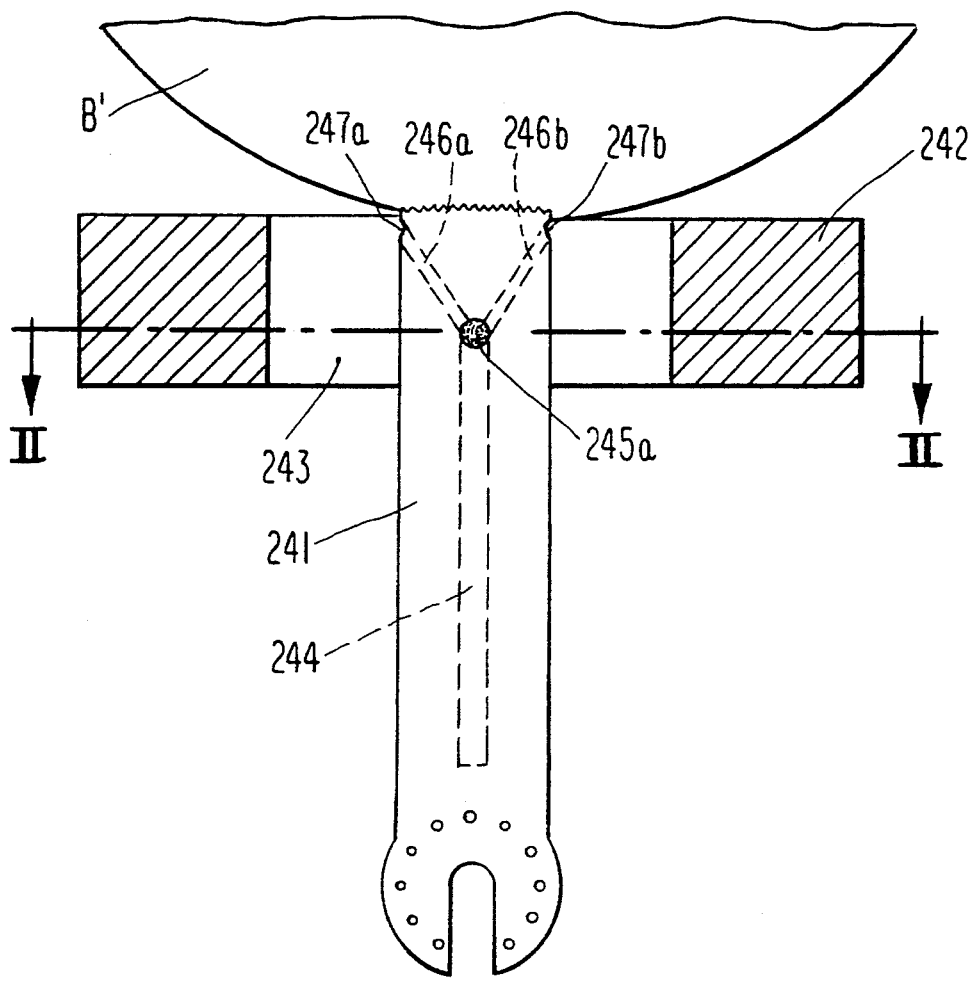
FIG. 8 is a top plan view of a bone shaping apparatus of the present invention, wherein the bone shaping member is disposed within a slotted surgical guide, and wherein porous plugs are located on the wide sides of the shaping member to provide lubricating fluid between the shaping member and the surgical guide.
Figure 9:
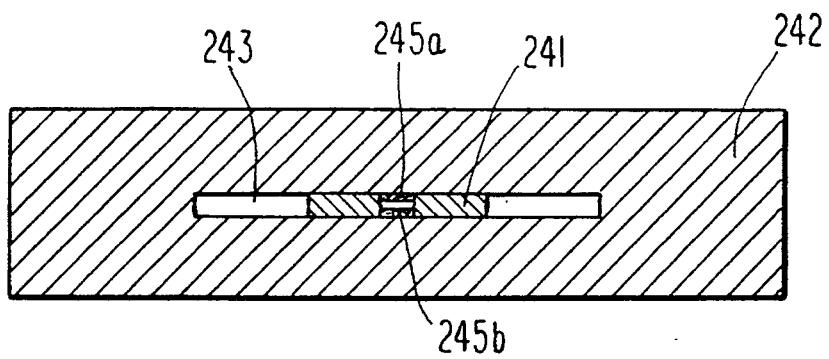
FIG. 9 is a sectional end view taken along line II—II of FIG. 8, illustrating the placement of the bone shaping member in the slotted surgical guide and the use of a porous medium for providing lubrication of the shaping member within the guide.

FIGS. 8 and 9 illustrate another embodiment of the present invention in which the bone shaping member is used in conjunction with a surgical guide. The shaping member 241 is disposed within a surgical guide 242 having a slotted opening 243. The bone to be shaped or cut is shown at B'. A conduit 244 extends longitudinally through the shaping member 241. At least one porous member 245a, 245b is in fluid flow communication between the conduit 244 and at least one exterior wide surface of the shaping member 241. The locations of the porous members 245a and 245b are such that, during a bone forming operation, fluid is supplied from a fluid source, through the conduit 244, through the porous members 245a and 245b to the space between the wide sides of the shaping member 241 and the slot 243 of the surgical guide 242. Fluid provided through the porous members 245a and 245b minimizes friction and reduces wear and subsequent fretting of saw blade material. Thus, heat build-up is kept to a minimum and abraded or fretted material is not introduced into the bone shaping area. The use of the porous members 245a and 245b as shown in FIGS. 8 and 9 is preferred because it eliminates jetting of cooling or lubricating fluid and allows the fluid to weep from the shaping member in a desired amount for friction control. While the use of such a porous member is preferred, it is recognized that a hole without the porous material may be used, but may be prone to jetting.

As shown in FIG. 8, the shaping member 241 may be provided with fluid conduits 246a and 246b that end in openings 247a and 247b, respectively, located at the narrow sides of the shaping member 241. Thus, fluid may be provided through conduit 244 to both the porous members 245a and 245b and the conduits 246a and 246b. An opening may be provided between the porous members 245a and 245b, as shown most clearly in FIG. 8, in order to allow increased fluid flow from the conduit 244 to the conduits 246a and 246b. Thus, most of the fluid supplied through the conduit 244 may be directed to the conduits 246a and 246b for introduction into the bone shaping area, while a lesser amount of the fluid may be absorbed through the porous members 245a and 245b to provide friction control.

When a surgical guide is not used during an operation, the porous members 245a and 245b may be replaced with solid plugs to eliminate the discharge of fluid from the wide side surfaces of the shaping member 241, if desired.

Figure 10:
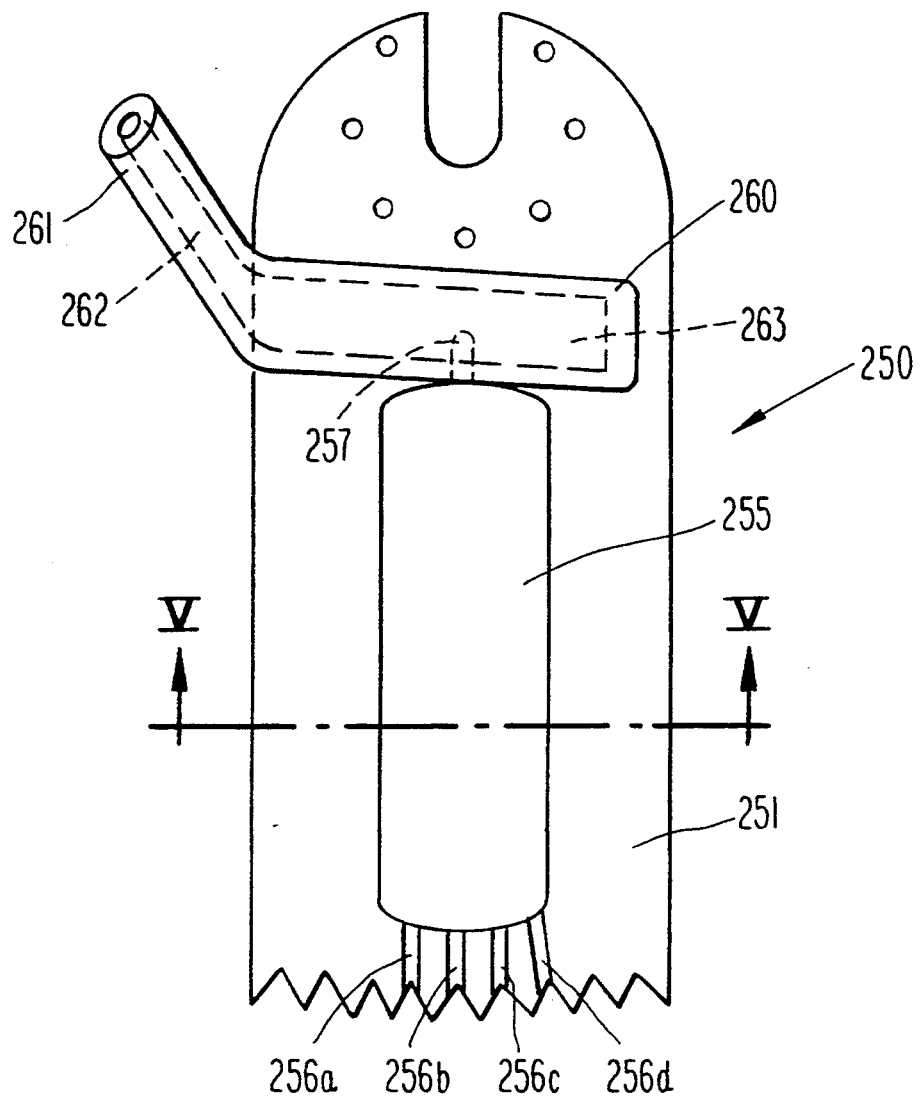
FIG. 10 is a top plan view of a bone shaping apparatus of the present invention, wherein an external fluid delivery channel is provided on the surface of the shaping member.
Figure 11:
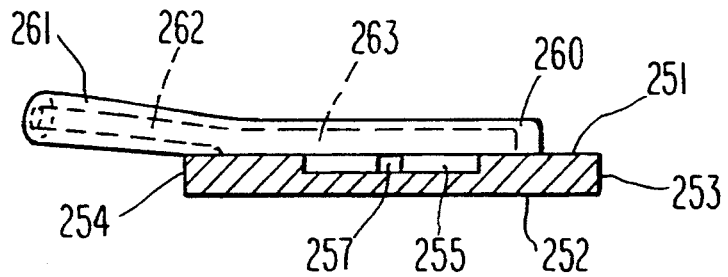
FIG. 11 is a sectional end view taken along line V—V of FIG. 10, showing a fluid delivery channel located on one exterior surface of the shaping member.

FIG. 10 is a plan view and FIG. 11 is a sectional end view of a bone shaping member in accordance with another embodiment of the present invention. The shaping member, shown generally at 250, includes two wide surfaces 251 and 252 connecting two narrow surfaces 253 and 254. An external fluid delivery channel 255 extends in a generally longitudinal direction along the external wide side surface 251 of the shaping member. The end of the exterior channel 255 proximate the cutting end of the shaping member may optionally be provided with grooves that extend from the end of the channel to the cutting teeth of the shaping member and may be placed on one or both wide surfaces. Such optional grooves are shown in FIG. 10 as elements 256a, 256b, 256c and 256d. As shown in FIG. 10, the optional grooves 256a, 256b, 256c and 256d are provided on only one wide side 251 of the shaping member in the gullets between adjacent cutting teeth.

Fluid is provided to the exterior channel 255 of the shaping member 250 via a fluid fitting 260. The fitting 260 includes a fluid delivery tube 261 having a fluid delivery line 262 therein. The fluid delivery line 262 extends at 263 across the wide side 251 of the shaping member and is in fluid flow communication with an orifice 257 that extends into the exterior channel 255. The fluid fitting 260 may be connected to the shaping member 250 by any suitable means, preferably by rivets, screws or other fasteners (not shown).

During operation, fluid is provided via the supply line 262 through the orifice 257 and into the exterior channel 255. It has been found, in accordance with the present invention, that by projecting a jet of water parallel to the surface of the shaping member into the channel 255, fluid can be carried all the way to the teeth of the shaping member. Even when the shaping member is inserted into the slot of a surgical guide, as shown in FIGS. 8 and 9, the fluid introduced into the external channel 255 is carried to the cutting teeth of the shaping member. While not intending to be bound by any particular theory, the mechanism that allows the cooling, curative, lubricating or other fluid to flow along the external channel 255 to the cutting teeth of the shaping member may be the Coanda effect, wherein the fluid introduced into the channel 255 tends to remain attached to the flat blade surface until it reaches the cutting teeth. In accordance with the present invention, it has been found that the fluid stream will adhere to the external channel 255 by virtue of the Coanda effect, even if the blade surface faces downward. Such an inverted position is actually preferred because when a slotted surgical guide is used, the lower surface of the slotted guide is the reference surface and the one most likely to experience high friction. Also, this orientation minimizes spray. Once the blade is enclosed by the slotted saw guide, the fluid stream will be contained and serve to lubricate the slotted saw guide (fixture) as well. Thus, when a slotted guide is used, the external channel 255 serves the dual function of providing fluid to the cut bone surface and lubricating the blade as it oscillates within the guide.

The depth, width and/or shape of the external channel 255 may be varied in order to optimize fluid delivery characteristics. Although it is currently preferred to provide an external channel on only one wide side surface of the shaping member, as shown in FIGS. 10 and 11, it is to be understood that external channels can be provided on both wide sides of the shaping member. While a single external channel 255 as shown in FIGS. 10 and 11 is most preferred, it is to be understood that multiple external channels may be provided on a single wide side surface.

Furthermore, while not currently preferred, the external channel can be provided as a slot to extend through the entire width of the shaping member. Thus, the depth of the channel 255 as shown in FIG. 11 can be increased to extend the entire distance from the wide side 251 to the wide side 252 of the shaping member. In this case, the channel 257 is used to project fluid in a jet-like manner toward the cutting end of the shaping member. Such an embodiment may be particularly useful where a surgical guide as shown in FIGS. 8 and 9 is used, wherein the surgical guide provides additional containment of the fluid.

Figure 12:
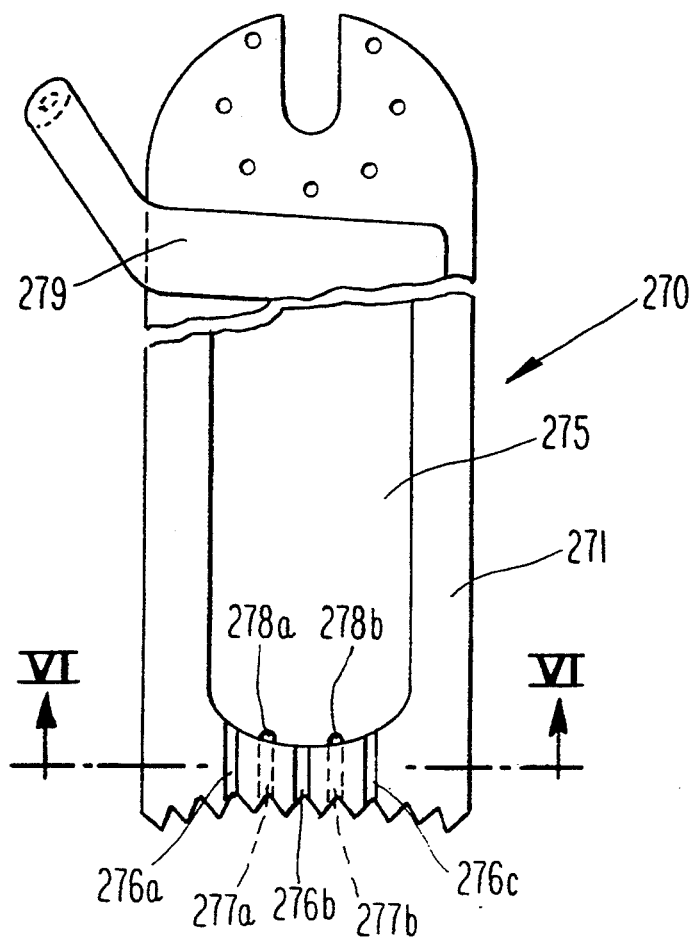
FIG. 12 is a top plan view of a bone shaping apparatus of the present invention, wherein a fluid delivery channel is provided on one wide exterior surface of the shaping member and grooves are provided on both wide sides of the member in fluid communication with the channel.
Figure 13:
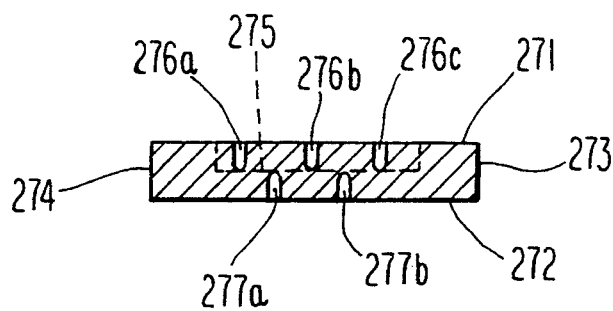
FIG. 13 is a sectional end view taken along line VI—VI of FIG. 12, showing grooves for fluid delivery and/or exhaust located on opposite wide sides of the shaping member.

FIG. 12 is a plan view and FIG. 13 is a sectional end view of a bone shaping member in accordance with a further embodiment of the present invention. The shaping member, shown generally at 270, includes two wide surfaces 271 and 272 connecting two narrow surfaces 273 and 274. An external fluid delivery channel 275 extends in a generally longitudinal direction along the external wide side surface 271 of the shaping member. The end of the exterior channel 275 proximate the cutting end of the shaping member is provided in communication with grooves on both wide sides 271 and 272 that extend from the end of the channel 275 to the cutting teeth of the shaping member. Grooves 276a, 276b and 276c are provided on the same side of the member as the external channel 275. Thus, fluid supplied to the channel 275 flows along the exterior surface of the channel into the grooves 276a, 276b and 276c, toward the shaping teeth. In addition, grooves 277a and 277b are provided on the opposite wide side of the member 272 from the external channel 275. As shown in FIG. 12, the grooves 277a and 277b extend for a sufficient length and depth to form portions 278a and 278b that are in fluid flow communication with the external channel 275. Thus, in accordance with the embodiment shown in FIGS. 12 and 13, fluid that is introduced into the external channel 275 via fluid fitting 279 flows by the Coanda effect to the grooves 276a, 276b, 276c, 277a and 277b, toward the shaping surface of the member.

The grooves as shown in FIG. 12 are preferably provided in the gullets between adjacent cutting teeth.

Fluid is provided to the exterior channel 275 of the shaping member 270 in a similar manner to that disclosed in the embodiment of FIGS. 10 and 11. Thus, the fluid fitting 279 may include a fluid delivery tube (not shown) having a fluid delivery line (not shown) therein. As in the embodiment of FIGS. 12 and 13, the fluid delivery line may be in fluid flow communication with an orifice (not shown) that extends into the exterior channel 275.

The shaping member of FIGS. 12 and 13 may also be used in combination with a slotted surgical guide as described above, whereby fluid supplied in the external channel 275 is additionally used to lubricate the shaping member as it slides within the guide.

The fluid delivery configuration as shown in FIGS. 12 and 13 posseses the advantage that fluid may be provided to the shaped bone surface via grooves along both wide sides 271 and 272 of the member. While it is presently preferred to deliver fluid in the grooves 276a, 276b, 276c, 277a and 277b, it is to be understood that at least one of the grooves may be used to exhaust fluid and debris from the bone shaping area. For example, the grooves provided on one wide side of the member may be used to introduce fluid to the shaping area, while the grooves provided on the opposite side of the member may be used to exhaust fluid and other material from the cutting zone. When the grooves are used to exhaust material, a vacuum source (not shown) may optionally be connected proximate the exhaust grooves to assist in debris removal.

The shaping member embodiments as shown in FIGS. 10-13 are particularly advantageous from a fabrication standpoint because the channels 255 and 275 are formed on the external surface of the shaping member. Since the channels remain uncovered, fabrication and assembly costs are significantly reduced.

Figure 14:
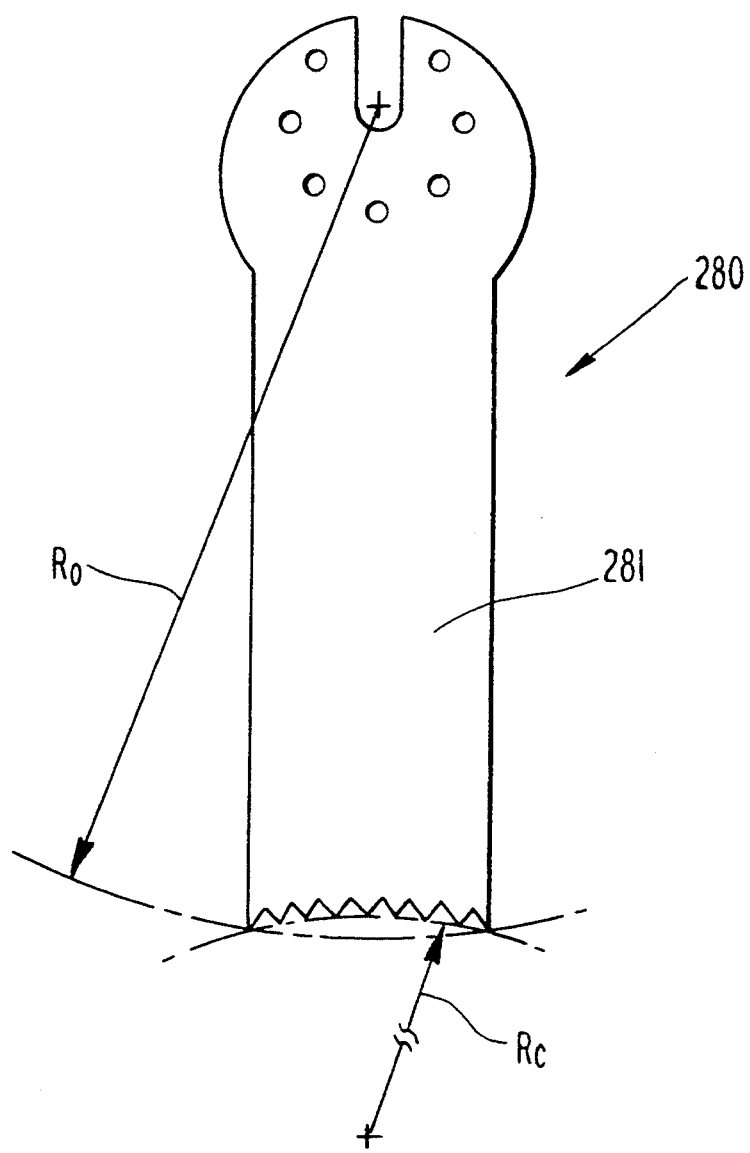
FIG. 14 is a top plan view of a concave tooth configuration of the present invention.

A particularly preferred cutting teeth configuration of the present invention is shown in FIG. 14. In this configuration, the teeth are provided in a concave orientation at the cutting end of the member 280. The radius of concavity $R_c$ can range from infinity, in which case the teeth are provided in a flat configuration, to one-half of the width of the wide side 281 of the blade. The blade 280 posseses a radius of oscillation $R_o$ about which the blade pivots to form an arc during operation. In a preferred embodiment, the radius of concavity $R_c$ is from one-half to two times the radius of oscillation $R_o$. In a particularly preferred embodiment, in which excellent cutting properties are achieved, the radius of concavity $R_c$ equals the radius of oscillation $R_o$.

As opposed to conventional convex teeth arrangements, the concave configuration as shown in FIG. 14 does not rely on the edge teeth to remove most of the material during cutting. In conventional concave designs, the center teeth cut little, if at all, and tend to pack with debris and to restrict the cutting of the end teeth during operation. In contrast, the concave teeth configuration of the present invention provides for predominant cutting on the instroke, with debris being hurled out of the teeth and cutting area on the outstroke. By using the present concave teeth configuration, superior cutting performance is achieved, such as higher speed and accuracy with lower bone temperatures.

The concave teeth configuration of FIG. 14 may be used with any of the shaping members previously described. Furthermore, each of the bone shaping member embodiments illustrated in FIGS. 7-14 may be used in conjunction with the aerosol control means described above. Thus, cooling, lubricating and/or curative fluids may be applied to the shaped bone surface, while at the same time providing for the control of aerosols generated during the bone shaping operation.

It will also be seen that the present invention provides a combination of fluid, as well as aerosol control, along with heat control for resulting in lower temperature shaping, insofar as the bone is concerned. Other details of the invention, its use and operation, selection of materials, and details of the delivery systems may all be provided in accordance with the present apparatus or modifications thereof, well within the spirit and scope of the invention as defined in the appended claims.

We claim:

1. An apparatus for shaping bone during surgical operations, the apparatus comprising:
   a) a bone shaping member having in transverse cross-section two wide sides each connecting two narrow sides and a length extending from a proximal end to a distal end;
   b) means on the shaping member for attachment of the member to a driving source for driving the member in shaping contact with bone;
   c) shaping means on the bone shaping member defining a shaping surface for shaping engagement with bone;
   d) at least one external channel located on at least one wide side of the shaping member adapted for providing fluid along the channel toward the shaping surface, said at least one external channel extending along the length of the bone shaping member and terminating short of the bone shaping member distal end at an external channel distal end, said at least one external channel being open to the external environment along the length of the channel;
   e) at least one groove means for facilitating fluid flow in fluid flow communication with the external channel and extending from the distal end of the external channel to the shaping means; and
   f) means carried by the shaping member for facilitating delivery of fluid to the at least one open external channel.

2. The apparatus of claim 1, wherein the external channel is provided on only one wide side of the bone shaping member.

3. The apparatus of claim 1, wherein the external channel is adapted for connection to a fluid supply by means of a fluid fixture.

4. The apparatus of claim 1, wherein the external channel is provided on only one wide side of the bone shaping member and is adapted for connection to a fluid supply by means of a fluid fixture fastened to the same wide side of the bone shaping member on which the channel is provided.

5. The apparatus of claim 1, wherein the external channel runs along most of the length of the at least one wide side of the shaping member.

6. The apparatus of claim 1, wherein the external channel does not have a cover disposed over any of the surface area thereof.

7. The apparatus of claim 1, wherein the at least one groove is provided on the same wide side as the external channel.

8. The apparatus of claim 1, wherein at least one of the grooves is provided on each wide side of the member.

9. The apparatus of claim 1, wherein the external channel is provided on only one wide side of the bone shaping member and a plurality of the grooves are provided on both wide sides of the member.

10. The apparatus of claim 1, wherein the bone shaping member is adapted for insertion in a slotted surgical guide and the external channel is adapted for providing controlled flow of fluid between the at least one wide side surface of the shaping member and the slot of the surgical guide.

11. The apparatus of claim 1, further comprising means on the shaping member for providing a fluid jet that adheres to a surface of the at least one open external channel to provide the fluid along the at least one open external channel toward the shaping surface.

12. The apparatus of claim 1, wherein the shaping surface is concave.

13. The apparatus of the claim 12, wherein the means for driving the member in shaping contact with bone comprises means for driving the member in oscillating shaping contact with bone about a radius of oscillation, and the concave shaping surface has a radius of concavity of from one-half to two times the radius of oscillation.

14. The apparatus of claim 13, wherein the radius of concavity is substantially equal to the radius of oscillation.

* * * * *